(12) United States Patent
Yamashita (10) Patent No.: US 9,541,015 B2
(45) Date of Patent: Jan. 10, 2017

(54) FUEL PROPERTY DETERMINATION APPARATUS FOR INTERNAL COMBUSTION ENGINE

(71) Applicant: TOYOTA JIDOSHA KABUSHIKI KAISHA, Toyota-shi (JP)

(72) Inventor: Akitaka Yamashita, Okazaki (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 0 days.

(21) Appl. No.: 14/813,568

(22) Filed: Jul. 30, 2015

(65) Prior Publication Data

US 2016/0032848 A1 Feb. 4, 2016

(30) Foreign Application Priority Data

Aug. 1, 2014 (JP) .................................. 2014-157707

(51) Int. Cl.
 *F02P 5/15* (2006.01)
 *G01N 33/26* (2006.01)
 (Continued)

(52) U.S. Cl.
 CPC ........... *F02D 37/02* (2013.01); *F02D 41/0025* (2013.01); *F02D 41/34* (2013.01); *F02P 5/045* (2013.01);
 (Continued)

(58) Field of Classification Search
 CPC ... G01N 33/2829; F02P 5/1506; F02P 5/1508; F02P 5/1527
 (Continued)

(56) References Cited

U.S. PATENT DOCUMENTS

| 6,276,131 | B1 * | 8/2001 | Ueno | ................... | F02D 31/003 |
| | | | | | 123/339.11 |
| 7,228,221 | B2 * | 6/2007 | Niimi | ................... | F02D 19/081 |
| | | | | | 123/339.11 |

(Continued)

FOREIGN PATENT DOCUMENTS

| JP | 10-331673 A | 12/1998 |
| JP | 2006-022722 A | 1/2006 |

(Continued)

OTHER PUBLICATIONS

Partial English Translation of Office Action mailed Aug. 3, 2016 in Japanese Patent Application No. 2014-157707.

*Primary Examiner* — Erick Solis
(74) *Attorney, Agent, or Firm* — Oblon, McClelland, Maier & Neustadt, L.L.P.

(57) ABSTRACT

A apparatus for an engine, and the apparatus includes an ECU. The ECU is configured to (i) perform a feedback control such that the engine speed converges to a target speed by correcting ignition timing during the feedback control, (ii) make a determination that fuel supplied to the engine is a heavy fuel when an ignition fulfillment rate is equal to or greater than a predetermined threshold value within a predetermined period after the engine is started, the ignition fulfillment rate is a ratio of the advance correction amount of the ignition timing to a maximum ignition correction range, the maximum ignition correction range is a maximum range in which the ignition timing is corrected during the feedback control, and (iii) set the threshold value to a value that depends on a temperature representative value of the engine, the temperature representative value is correlated with the engine temperature.

5 Claims, 5 Drawing Sheets

(51) Int. Cl.
  *F02D 37/02* (2006.01)
  *F02P 5/152* (2006.01)
  *G01N 33/28* (2006.01)
  *F02D 41/34* (2006.01)
  *F02P 5/04* (2006.01)
  *F02D 41/00* (2006.01)

(52) U.S. Cl.
  CPC ............ *F02P 5/1506* (2013.01); *F02P 5/1508* (2013.01); *F02P 5/1527* (2013.01); *G01N 33/2829* (2013.01); *F02D 2200/021* (2013.01); *F02D 2200/023* (2013.01); *F02D 2200/0612* (2013.01); *Y02T 10/46* (2013.01)

(58) Field of Classification Search
  USPC ............ 701/103; 123/339.11, 406.3, 406.31, 123/406.59; 73/35.02, 35.03, 114.08
  See application file for complete search history.

(56) References Cited

U.S. PATENT DOCUMENTS

| | | | | |
|---|---|---|---|---|
| 7,997,063 | B2* | 8/2011 | Thanasiu | F01N 11/007 123/1 A |
| 8,447,498 | B2* | 5/2013 | Toyohara | F02D 31/008 123/339.11 |
| 2003/0168041 | A1* | 9/2003 | Kubo | F02D 11/105 123/339.11 |
| 2004/0255902 | A1* | 12/2004 | Sawada | F02D 31/001 123/339.11 |
| 2008/0162017 | A1 | 7/2008 | Nagata et al. | |

FOREIGN PATENT DOCUMENTS

| | | |
|---|---|---|
| JP | 3863362 | 12/2006 |
| JP | 4356079 | 11/2009 |
| JP | 2010-144599 A | 7/2010 |
| WO | 2006/027853 A1 | 3/2006 |

* cited by examiner

FIG. 1

AT START-UP OF INTERNAL
COMBUSTION ENGINE USING REGULAR FUEL
(AT NORMAL TEMPERATURE)

TARGET SPEED (NT)

ENGINE SPEED (NE)

IGNITION TIMING CORRECTION AMOUNT (anefb)

HEAVY FUEL DETERMINATION THRESHOLD VALUE (Ch)

IGNITION FULFILLMENT RATE (anefbrte)

HEAVY FUEL DETERMINATION FLAG

OFF

FUEL PROPERTY DETERMINATION APPARATUS FOR INTERNAL COMBUSTION ENGINE

INCORPORATION BY REFERENCE

The disclosure of Japanese Patent Application No. 2014-157707 filed on Aug. 1, 2014 including the specification, drawings and abstract is incorporated herein by reference in its entirety.

BACKGROUND OF THE INVENTION

1. Field of the Invention

The present invention relates to a fuel property determination apparatus for an internal combustion engine.

2. Description of Related Art

It is known that the properties of the fuel that is supplied to an internal combustion engine has an influence on the control of such things as the air-fuel ratio in the internal combustion engine. For example, because a heavy fuel has a lower volatility than a regular fuel, any control that is designed for a regular fuel may adversely affect the operability and/or exhaust emission of the internal combustion engine if performed when a heavy fuel is being used. Various attempts have been made to determine fuel properties so that control of an internal combustion engine suitable for the fuel properties can be achieved.

Japanese Patent No. 3863362 discloses an internal combustion engine that is equipped with ignition timing control means that performs feedback control of the ignition timing so that the engine speed of the internal combustion engine can converge to a target speed during idling after start-up. It is disclosed in Japanese Patent No. 3863362 that an ignition timing correction amount at a time when the engine speed is stabilized with respect to a target speed and an ignition timing correction amount at which the engine speed converges after the stabilization are calculated and fuel properties are determined based on the difference between the ignition timing correction amounts.

It is also known that a more accurate determination of fuel properties is made based on the ratio of the correction amount from a basic ignition timing corresponding to a target speed (which may be hereinafter referred to as "ignition timing correction amount") to the allowable range of the ignition timing that is determined depending on the target speed, temperature and so on of the internal combustion engine (which may be hereinafter referred to as "maximum ignition correction range").

Japanese Patent No. 4356079 discloses a fuel property determination apparatus that determines fuel properties based on a combustion parameter that is calculated based on the pressure in a cylinder of an internal combustion engine (the length of combustion period). It is disclosed in Japanese Patent No. 4356079 that the threshold value that is used to make a determination of fuel properties is set based on the temperature of the internal combustion engine to make a more accurate determination of fuel properties.

As described above, various attempts have been made to determine fuel properties so that control of an internal combustion engine suitable for the fuel properties can be achieved. It is also known that a more accurate determination of fuel properties is made based on the ratio of the ignition timing correction amount to the maximum ignition correction range. When control of air-fuel ratio and so on is performed based on fuel properties in this way, the operability and/or exhaust emission of the internal combustion engine can be maintained in a favorable condition.

SUMMARY OF THE INVENTION

However, when the temperature of the internal combustion engine is low in, for example, a cold district, an erroneous determination that the fuel is a heavy fuel may be made by the fuel property determination method as described above even when the fuel that is being used is actually a regular fuel.

The present invention provides a fuel property determination apparatus for an internal combustion engine which can make an accurate determination of whether the fuel that is being supplied to the internal combustion engine is a heavy fuel even at low temperatures.

A first aspect of the present invention provides a fuel property determination apparatus for an internal combustion engine, the internal combustion engine including a spark plug, the spark plug including a spark generating portion. The fuel property determination apparatus includes a electronic control unit. The electronic control unit is configured to perform a feedback control such that the engine speed converges to a target speed by correcting ignition timing during the feedback control, the ignition timing being a timing when the spark generating portion generates a spark. The electronic control unit is configured to make a determination that the fuel supplied to the internal combustion engine is a heavy fuel when an ignition fulfillment rate is equal to or greater than a predetermined threshold value within a predetermined period the internal combustion engine is started, the ignition fulfillment rate is a ratio of the advance correction amount of the ignition timing to a maximum ignition correction range, the maximum ignition correction range is a maximum range of a correction range in which the ignition timing is corrected during the feedback control. The electronic control unit is configured to set the threshold value to a value that depends on a temperature representative value of the internal combustion engine, the temperature representative value is correlated with the temperature of the internal combustion engine.

In the fuel property determination apparatus, the temperature representative value may have a positive correlation with the temperature of the internal combustion engine, and the electronic control unit may be configured to set the threshold value to a greater value as the temperature representative value is smaller.

The fuel property determination apparatus may further include a coolant temperature sensor. The coolant temperature sensor may be configured to detect a temperature of coolant in the internal combustion engine. The electronic control unit may be configured to use the temperature of coolant as the temperature representative value, the temperature of coolant is detected by the coolant temperature sensor when the internal combustion engine is started.

The fuel property determination apparatus may further include an oil temperature sensor. The oil temperature sensor may be configured to detect a temperature of lubricating oil in the internal combustion engine. The electronic control unit may be configured to use the temperature of lubricating oil as the temperature representative value, the temperature of the lubricating oil is detected by the oil temperature sensor when the internal combustion engine is started.

The fuel property determination apparatus may further include a refuel sensor. The refuel sensor may be configured to detect a refuel operation. The electronic control unit may be configured to discard the result of the determination of fuel property when a refuel operation is detected by the refuel sensor, and the electronic control unit may be configured to prohibit the execution of the determination when the fuel is determined as a heavy fuel.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

In one embodiment of the present invention, the maximum ignition correction range is the allowable range of the ignition timing that is determined depending on the target speed, temperature and so on of the internal combustion engine of the moment. In other words, the maximum ignition correction range is the range of ignition timing that is determined by the difference between the most advanced ignition timing absef and the most retarded ignition timing aopmn at which stable idling operation can be achieved at the target speed, temperature and so on of the internal combustion engine of the moment. The ignition fulfillment rate is, as described above, the ratio of the advance correction amount of the ignition timing to the maximum ignition correction range. In other words, the ignition fulfillment rate is the proportion of the correction amount of the ignition timing to the advance side to the range in which the ignition timing can be changed. Thus, when the ignition timing is corrected to the retard side, the ignition fulfillment rate is 0 (zero).

When fuel properties are determined based on the ratio of an ignition timing correction amount to the maximum ignition correction range, such as the above-mentioned ignition fulfillment rate, an erroneous determination that the fuel is a heavy fuel may be made in an internal combustion engine immediately after a cold start even when the fuel that is being used is actually a regular fuel.

Figure 1:
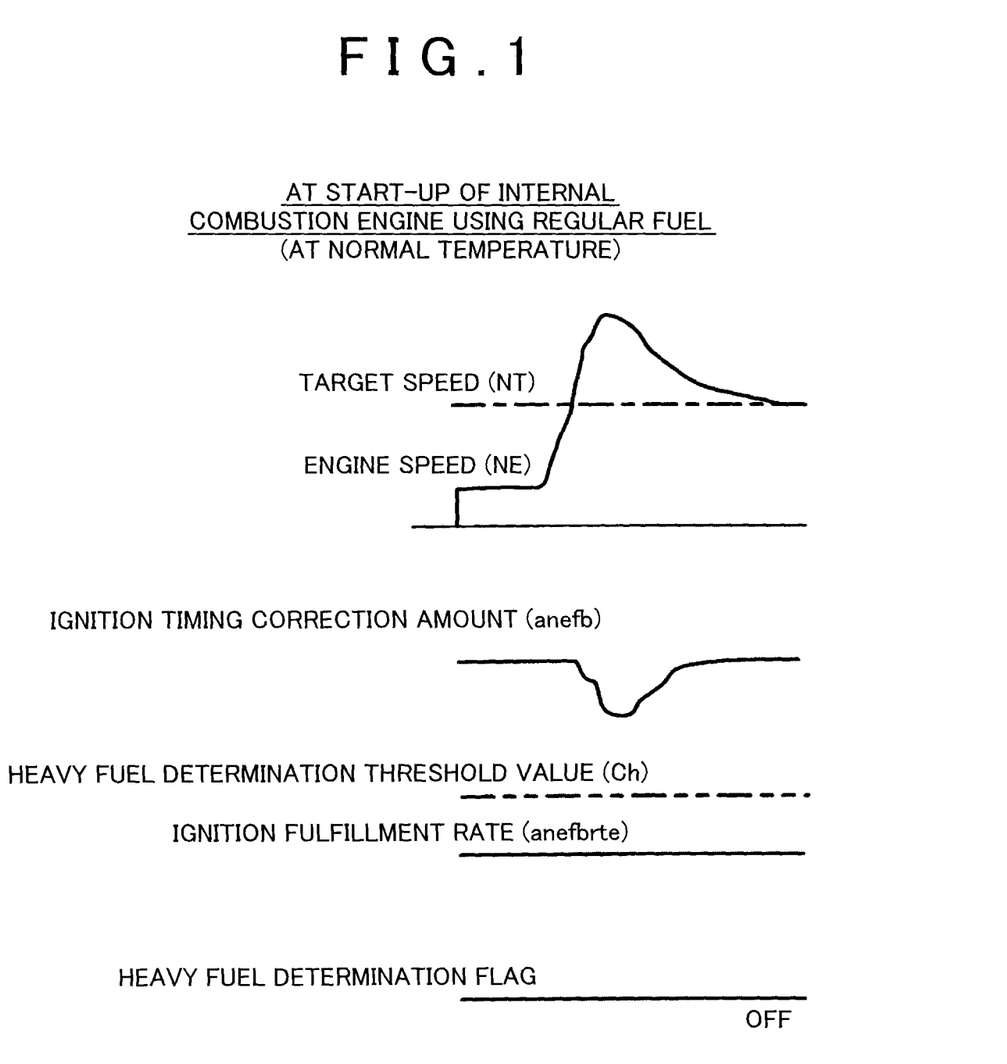
FIG. 1 is a schematic time chart that shows how the engine speed, the ignition timing correction amount, the ignition fulfillment rate and the heavy fuel determination flag, which is a flag that indicates that the fuel is a heavy fuel, change at normal temperature within a predetermined period after start-up of an internal combustion engine that is using a regular fuel.
Figure 2:
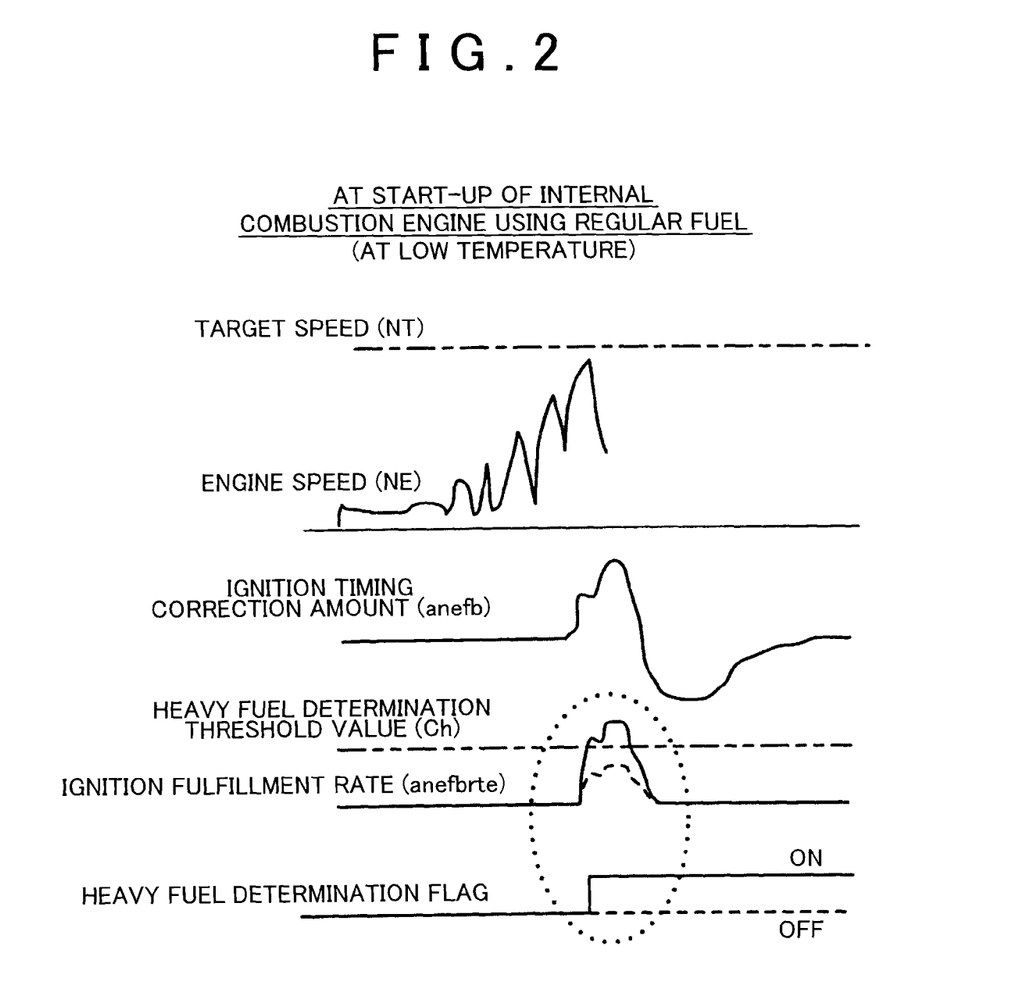
FIG. 2 is a schematic time chart that shows how the engine speed, the ignition timing correction amount, the ignition fulfillment rate and the heavy fuel determination flag, which is a flag that indicates that the fuel is a heavy fuel, change at a low temperature within a predetermined period after start-up of an internal combustion engine that is using a regular fuel.

This erroneous determination is described below with reference to FIG. 1 to FIG. 5. FIG. 1 is a schematic time chart that shows how the engine speed NE, the ignition timing correction amount (anefb), the ignition fulfillment rate (anefbrte) and the heavy fuel determination flag, which is a flag that indicates that the fuel is a heavy fuel, change at normal temperature within a predetermined period after start-up of an internal combustion engine that is using a regular fuel (the internal combustion engine is started). FIG. 2 shows how these change at a low temperature.

As shown in FIG. 1, in an internal combustion engine that is using a regular fuel, the engine speed NE increases quickly after start-up and exceeds the target speed NT (dot-and-dash line) at normal temperature. Then, the ignition timing is corrected to the retard side by the above-mentioned feedback control and the engine speed NE therefore starts to decrease. When the engine speed NE starts to decrease, the retard correction amount of the ignition timing is reduced and the engine speed NE soon converges to the target speed NT. In this period, the ignition fulfillment rate remains at 0 (zero) because the ignition timing is not corrected to the advance side. Thus, the ignition fulfillment rate does not increase to or exceed the heavy fuel determination threshold value Ch, which is a threshold value that is used to make a determination of whether the fuel is a heavy fuel. As a result, the heavy fuel determination flag is kept OFF.

On the other hand, even in an internal combustion engine that is using a regular fuel, the engine speed NE does not increase quickly after start-up at a low temperature as shown in FIG. 2. The engine speed NE increases gradually with repeated increases and decreases but does not easily reach the target speed NT (dot-and-dash line). After that, when the feedback control is started and the ignition timing is corrected to the advance side, the engine speed NE eventually exceeds the target speed NT. Then, the ignition timing is corrected to the retard side and the engine speed NE starts to decrease. When the engine speed NE starts to decrease, the retard correction amount of the ignition timing is reduced and the engine speed NE soon converges to the target speed NT. In the example that is shown in FIG. 2, as shown in the part encircled by a dotted ellipse, the ignition fulfillment rate (solid line) increases well over the heavy fuel determination threshold value Ch. As a result, the heavy fuel determination flag is switched to ON. In other words, in this case, an erroneous determination that a heavy fuel is being used is made despite the fact that a regular fuel is actually being used.

The present inventors conducted intensive studies for the purpose of reducing erroneous determinations as described above, and, consequently, found one of the causes of the erroneous determination. That is, even when the ignition timing correction amount is constant, a greater ignition fulfillment rate can be calculated as the temperature of the internal combustion engine is lower.

In some cases, the maximum ignition correction range decreases as the temperature of the internal combustion engine is lower. As described above, the ignition fulfillment rate is the ratio of the advance correction amount of the ignition timing to the maximum ignition correction range. Thus, a higher ignition fulfillment rate is calculated as the maximum ignition correction range decreases. Accordingly, a greater ignition fulfillment rate can be calculated as the temperature of the internal combustion engine is lower even when the ignition timing correction amount is constant.

Figure 3:
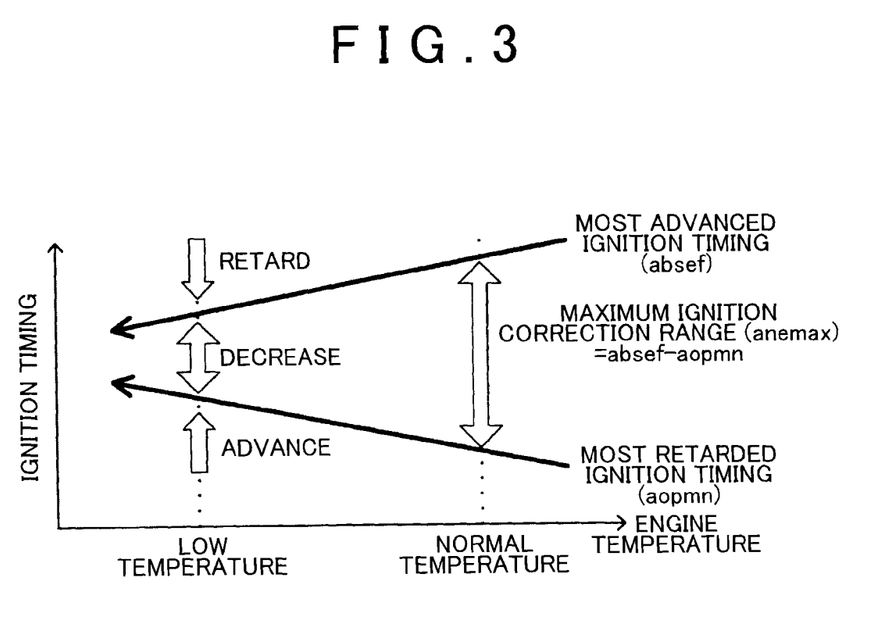
FIG. 3 is a schematic diagram that shows how the most advanced ignition timing and the most retarded ignition timing change with changes in the temperature of the internal combustion engine.
Figure 4:
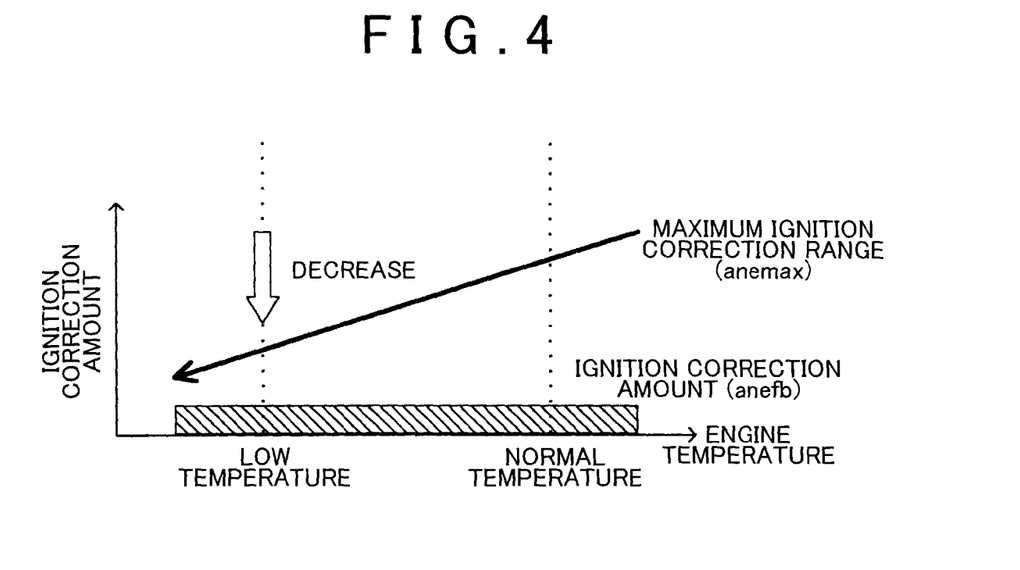
FIG. 4 is a schematic diagram that shows how the maximum ignition correction range changes with changes in the temperature of the internal combustion engine.
Figure 5:
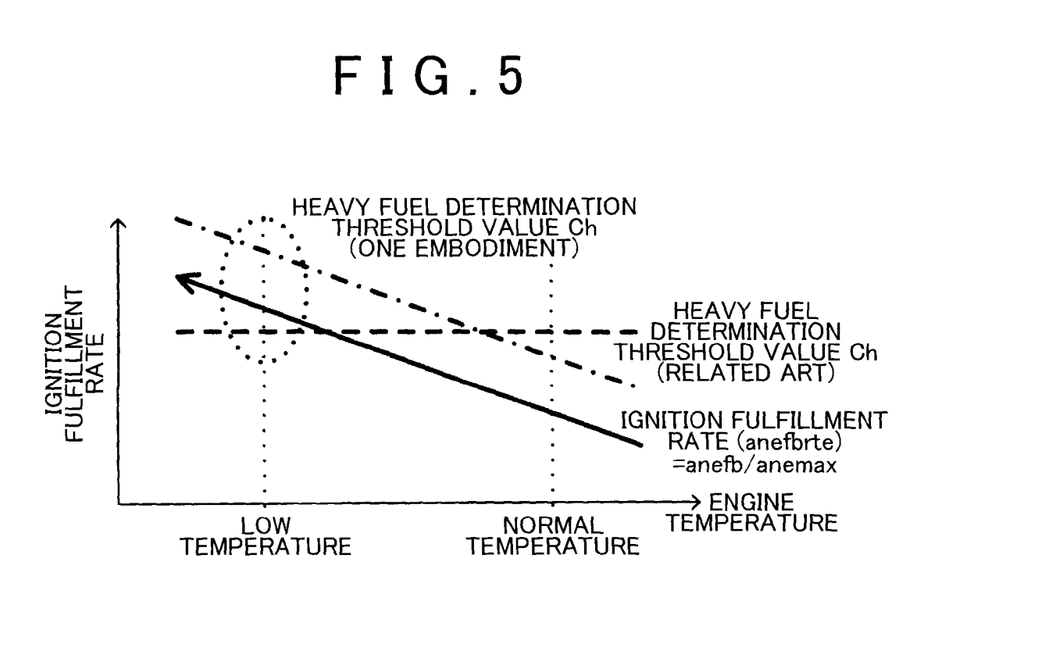
FIG. 5 is a schematic diagram that shows how the ignition fulfillment rate changes with changes in the temperature of the internal combustion engine.

The present inventors investigated the reason why the maximum ignition correction range decreases as the temperature of the internal combustion engine is lower. The result of investigation is described in detail below with reference to the appended drawings. FIG. 3 to FIG. 5 are schematic diagrams that respectively show how the most advanced ignition timing (ansef) and the most retarded ignition timing (anopmn), the maximum ignition correction range (anemax), and the ignition fulfillment rate (anefbrte) change with changes in the temperature of the internal combustion engine.

As the engine temperature decreases, the volatility of the fuel also decreases and it therefore takes longer time to form a combustible air-fuel mixture. Thus, in an internal combustion engine, the ignition timing on the most advanced side (the most advanced ignition timing absef) at which a stable idling operation can be achieved at the target speed, temperature and so on of the internal combustion engine of the moment is shifted more toward the retard side as the temperature of the internal combustion engine (which may be hereinafter referred to as "engine temperature") is lower as shown in FIG. 3.

In addition, in an internal combustion engine, when the temperature of the exhaust gas control catalyst that is provided to reduce harmful substances in the exhaust gas from the internal combustion engine is low, the ignition timing is corrected to the retard side for temperature rise (warm-up) of the exhaust gas control catalyst (catalyst warm-up retardation). When catalyst warm-up retardation is carried out in this way, the proportion of the amount of heat that is consumed for temperature rise (warm-up) of the internal combustion engine to the total amount of heat that is generated by combustion of fuel in the combustion chamber of the internal combustion engine decreases and the proportion of the amount of heat that is consumed for temperature rise (warm-up) of the exhaust gas control catalyst increases. As a result, the exhaust gas control catalyst can be increased in temperature (warmed up).

However, if catalyst warm-up retardation is carried out when the engine temperature is low, the temperature rise (warm-up) of the internal combustion engine delays because the proportion of the amount of heat that is consumed for temperature rise (warm-up) of the internal combustion engine to the total amount of heat that is generated by combustion of fuel decreases as described above. As a result, the operability and/or exhaust emission of the internal combustion engine may be adversely affected. Thus, in an internal combustion engine, catalyst warm-up retardation is limited when the engine temperature is low. Specifically, the ignition timing on the most retarded side (the most retarded ignition timing aopmn) at which a stable idling operation can be achieved at the target speed, temperature and so on of the internal combustion engine of the moment is shifted more toward the advance side as the engine temperature is lower as shown in FIG. 3.

As described above, the most advanced ignition timing absef is shifted more toward the retard side and the most retarded ignition timing aopmn is shifted more toward the advance side as the engine temperature is lower. As a result, as indicated by the outlined double-headed arrow in FIG. 3 and the diagonally left down arrow in FIG. 4, the maximum ignition correction range, which is the difference between those ignition timings, decreases as the engine temperature is lower. Thus, even when the ignition correction amount anefb is constant as indicated in the hatched portion of FIG. 4, the ignition fulfillment rate anefbrte increases as the engine temperature is lower as indicated by the diagonally left up arrow in FIG. 5.

The case where the most advanced ignition timing absef is shifted more toward the retard side and the most retarded ignition timing aopmn is shifted more toward the advance side as the engine temperature is lower is described with reference to FIG. 2. However, the fact that the maximum ignition correction range decreases as the engine temperature is lower remains the same even when the most advanced ignition timing absef is shifted more toward the retard side or the most retarded ignition timing aopmn is shifted more toward the advance side as the engine temperature is lower.

In a fuel property determination apparatus for an internal combustion engine according to a related art, the threshold value Ch that is used to make a determination of whether the fuel is a heavy fuel is set to a constant value regardless of whether the engine temperature is high or low as indicated by the broken line in FIG. 5. Thus, when the engine temperature is low as described above, the ignition fulfillment rate anefbrte can be so high as to reach a value equal to or greater than the threshold value Ch as indicated in the part encircled by a dotted line in FIG. 5. As a result, an erroneous determination that the fuel is a heavy fuel is made. In other words, in the fuel property determination apparatus of a related art, an erroneous determination that the fuel is a heavy fuel may be made when the engine temperature is low, such as immediately after a cold start, even when the fuel that is being used is actually a regular fuel.

In contrast, in the fuel property determination apparatus according to one embodiment of the present invention, an electronic control unit is configured to set the threshold value Ch to a value that depends on an engine temperature representative value that has a correlation with the temperature of the internal combustion engine. In the example that is shown in FIG. 5, the threshold value Ch is set to a greater value as the engine temperature is lower as indicated by a dot-and-dash line. Thus, as indicated in the part encircled by a dotted line in FIG. 5, the ignition fulfillment rate does not reach a value equal to or greater than the threshold value Ch and an erroneous determination that the fuel is a heavy fuel is prevented from being made. In other words, in this embodiment, a regular fuel is not erroneously determined to be a heavy fuel (for example, in the example that is shown in FIG. 2, the ignition fulfillment rate (broken line) does not reach the heavy fuel determination threshold value Ch as indicated in the part encircled by a dotted ellipse) even when the engine temperature is low, such as immediately after a cold start.

As described above, in the above embodiment, the threshold value Ch that is used to make a determination of whether the fuel that is being supplied to the internal combustion engine is a heavy fuel is set to a value that depends on an engine temperature representative value that has a correlation with the temperature of the internal combustion engine. Then, a determination that the fuel that is being supplied to the internal combustion engine is a heavy fuel is made if the ignition fulfillment rate is equal to or greater than the threshold value Ch when feedback control of the ignition timing is performed so that the engine speed of the internal combustion engine can converge to a target speed within a predetermined period after start-up of the internal combustion engine. As a result, the inventive apparatus can make a more accurate determination of whether the fuel that is being supplied to the internal combustion engine is a heavy fuel even at low temperatures.

A fuel property determination apparatus for an internal combustion engine (which may be hereinafter referred to as "determination apparatus") according to each embodiment of the present invention is hereinafter described with reference to the drawings.

A fuel property determination apparatus according to a first embodiment (which is hereinafter referred to simply as "first apparatus") is described below.

Figure 6:
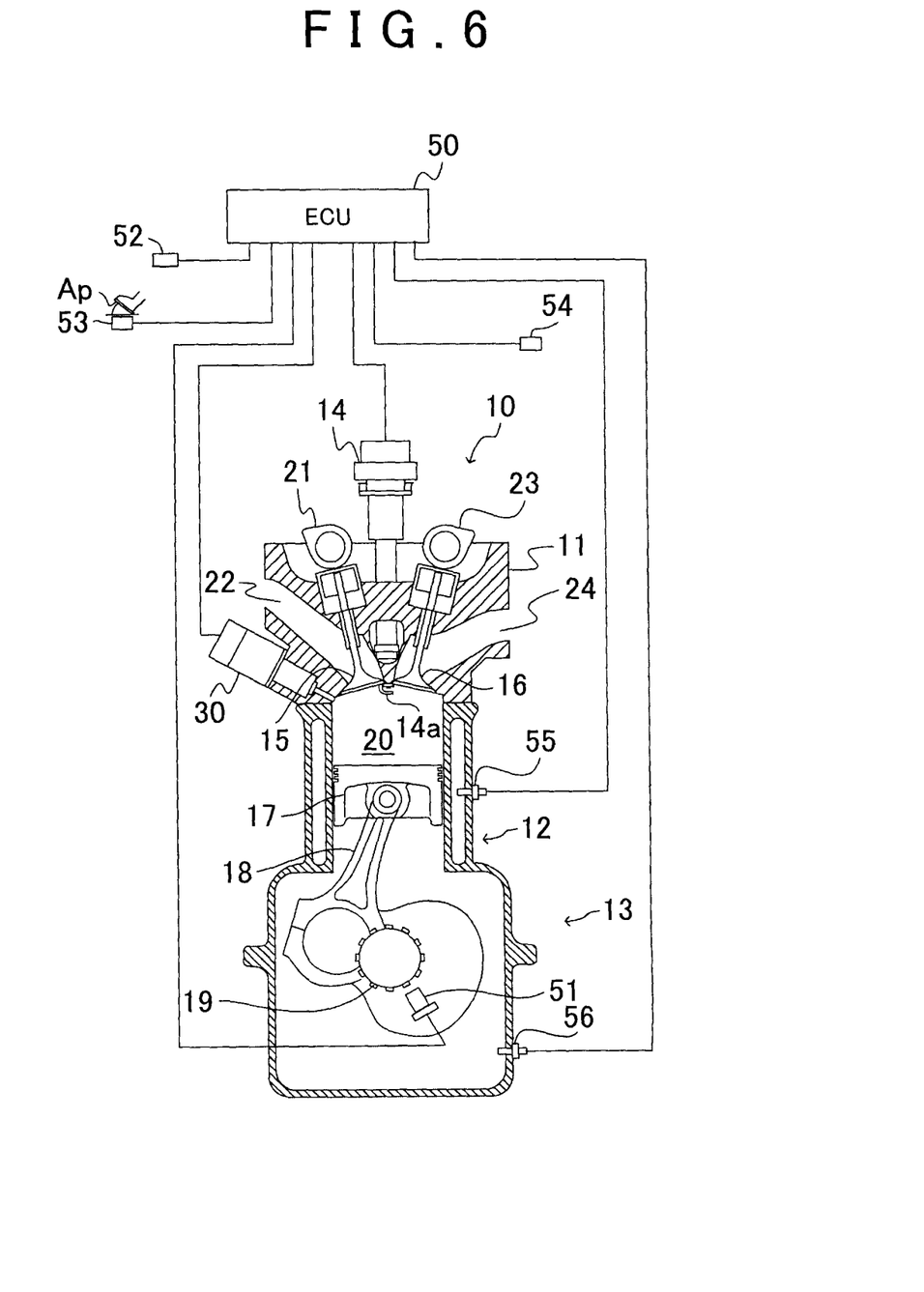
FIG. 6 is a schematic diagram that illustrates an internal combustion engine to which a fuel property determination apparatus for an internal combustion engine according to a first embodiment of the present invention (first apparatus) is applied.

(Configuration of internal combustion engine) The first apparatus is applied to an internal combustion engine (which is hereinafter referred to as "engine") 10 that is shown in FIG. 6.

The engine 10 is a gasoline-fuel spark-ignition engine. The engine 10 includes a cylinder head 11, a cylinder block 12, a crank case 13, a spark plug 14, an intake valve 15, an exhaust valve 16, a piston 17, a connecting rod 18, a crankshaft 19 and so on. A combustion chamber 20 is defined by a lower wall of the cylinder head 11, the wall of a cylinder bore that is formed in the cylinder block 12 and the crown top of the piston 17.

The spark plug 14 is installed in the cylinder head 11 with its spark generating portion 14a exposed at the center of the upper wall of the combustion chamber 20. The intake valve 15 is installed in the cylinder head 11 so that it can open and close a communication passage between the combustion chamber 20 and an intake port 22 that is formed through the cylinder head 11 when driven by an intake cam 21. The exhaust valve 16 is installed in the cylinder head 11 so that it can open and close a communication passage between the combustion chamber 20 and an exhaust port 24 that is formed through the cylinder head 11 when driven by an exhaust cam 23. The engine 10 is also equipped with a fuel injection valve (in-cylinder injection valve) 30. The fuel injection valve 30 is installed in a part between the intake port 22 of the cylinder head 11 and the cylinder block 12 so that it can inject a fuel into the combustion chamber 20.

As described above, the engine 10 that is shown in FIG. 6 is what is called a side injection-type internal combustion engine, in which the fuel injection valve 30, which is installed in a part between the intake port 22 of the cylinder head 11 and the cylinder block 12, injects fuel toward the central axis of the cylinder. However, the first apparatus can be applied not only to such a side injection-type internal combustion engine but also to what is called a center injection-type internal combustion engine in which fuel is injected from a fuel injection valve installed in the vicinity of the center of the cylinder head 11 toward the crown top of the piston 17, for example. Further, the first apparatus can be applied not only to such in-cylinder injection-type internal combustion engines but also to what is called a port injection-type internal combustion engine in which fuel is injected from a fuel injection valve that is installed in the intake port 22 of the cylinder head 11, for example.

The engine 10 is equipped with an electronic control unit (ECU) 50. The ECU 50 performs feedback control to correct the ignition timing, the timing of the spark generating portion 14a generating a spark, so that the engine speed NE can converge to a target speed NT.

(Configuration of ECU) The ECU 50 is a well-known microcomputer that includes a CPU, a ROM, a RAM, a backup RAM and so on. The ECU 50 is electrically connected to the spark plug 14, the fuel injection valve 30 and so on and sends drive signals to them. In addition, the ECU 50 is electrically connected to a crank position sensor 51, an air flow meter 52, an accelerator pedal depression amount sensor 53, an air-fuel ratio sensor 54, a coolant temperature sensor 55, an oil temperature sensor 56 and so on and receives signals from them.

The crank position sensor 51 generates a signal depending on the rotational position of the crankshaft 19. The ECU 50 calculates the engine speed NE based on the signals from the crank position sensor 51. In addition, the ECU 50 acquires an absolute crank angle on the basis of for example, the compression top dead center in any cylinder based on signals from the crank position sensor 51 and a cam position sensor (not shown). The air flow meter 52 generates a signal that indicates the flow rate of intake air into the engine 10. The accelerator pedal depression amount sensor 53 generates a signal that indicates the amount of depression of an accelerator pedal Ap. The air-fuel ratio sensor 54 generates a signal that indicates the air-fuel ratio of exhaust gas. The coolant temperature sensor 55 generates a signal that indicates the temperature of the coolant (coolant temperature) that is flowing through a water jacket that is provided around the cylinder block 12. The oil temperature sensor 56 generates a signal that indicates the temperature of the lubricating oil (oil temperature) in the oil pan at the bottom of the crank case 13.

(Configuration and operation of first apparatus) In the first apparatus, the ECU 50 calculates the ignition fulfillment rate, the ratio of the advance correction amount of the ignition timing to the maximum ignition correction range, within a predetermined period after start-up of the engine 10. The maximum ignition correction range is the maximum range in which the ignition timing can be corrected when the ECU 50 corrects the ignition timing during feedback control.

The ECU 50 makes a determination that the fuel that is being supplied to the engine 10 is a heavy fuel if the ignition fulfillment rate is equal to or greater than a predetermined threshold value Ch. The ECU 50 of the first apparatus is configured to set the threshold value Ch to a value that depends on an engine temperature representative value that has a correlation with the temperature of the engine 10. As the engine temperature representative value, a parameter that has a correlation with the temperature of the engine 10, for example, can be employed from among various parameters (operating condition parameters) that indicate the operating conditions of the engine 10.

The correspondence relationship between the operating condition parameter that is employed as the engine temperature representative value and the threshold value Ch can be identified in advance in, for example, a preliminary experiment using the engine 10 and stored as a map in, for example, a data storage device of the ECU 50. More specifically, the changes in the maximum ignition correction range with changes in the operating condition parameter that is employed as the engine temperature representative value are measured and a map (data table) that represents the correspondence relationship between them is stored in the ROM of the ECU 50 so that the set value of the threshold value Ch can be determined with reference to the map in making a determination of fuel properties, for example.

As described above, in the first apparatus, the threshold value Ch is set to a value that depends on an engine temperature representative value that has a correlation with the temperature of the engine 10. The threshold value is used to make a determination of whether the fuel that is being supplied to the engine 10 is a heavy fuel. Then, the first apparatus makes a determination that the fuel that is being supplied to the engine 10 is a heavy fuel if the ignition fulfillment rate is equal to or greater than the threshold value Ch when it performs feedback control of the ignition timing so that the engine speed NE of the engine 10 can converge to a target speed NT within a predetermined period after start-up of the engine 10. As a result, the first apparatus can make a more accurate determination of whether the fuel that is being supplied to the engine 10 is a heavy fuel even at low temperatures.

A determination apparatus according to a second embodiment (which is hereinafter referred to simply as "second apparatus") is next described. The second apparatus of this embodiment is different from the first apparatus only in that the engine temperature representative value has a positive correlation with the temperature of the engine 10 and in that the ECU 50 sets the threshold value Ch to a greater value as the engine temperature representative value is smaller.

Referring to FIG. 3, the most advanced ignition timing absef is shifted more toward the retard side and the most retarded ignition timing aopmn is shifted more toward the advance side as the temperature of the engine 10 is lower (the engine temperature representative value is smaller) as described above. As a result, the maximum ignition correction range, which is the difference between those ignition timings, decreases as the temperature of the engine 10 is lower (the engine temperature representative value is smaller). Thus, even when the ignition correction amount anefb is constant, the ignition fulfillment rate anefbrte increases as the temperature of the engine 10 is lower (the engine temperature representative value is smaller).

As described above, in the second apparatus, an engine temperature representative value that has a positive correlation with the temperature of the internal combustion engine is employed. In the second apparatus, the ECU 50 sets the threshold value Ch to a greater value as the engine temperature representative value is smaller. Thus, the second apparatus can more reliably reduce the possibility that an erroneous determination that the fuel is a heavy fuel is made despite the fact that a regular fuel is being used even when the ignition fulfillment rate anefbrte increases as the temperature of the engine 10 is lower (engine temperature representative value is smaller) as described above. In other words, the second apparatus can make a more accurate determination of whether the fuel that is being supplied to the internal combustion engine is a heavy fuel even at low temperatures.

A determination apparatus according to a third embodiment of the present invention (which is hereinafter referred to simply as "third apparatus") is described below. The third apparatus of this embodiment is different from the first and second apparatuses only in that the ECU 50 uses the temperature of coolant that has been detected by the coolant temperature sensor 55 at start-up of the engine 10 as the engine temperature representative value.

As described above, the ECU 50 of this embodiment is configured to set the threshold value Ch to a value that depends on an engine temperature representative value that has a correlation with the temperature of the engine 10. As the engine temperature representative value, a parameter that has a correlation with the temperature of the engine 10, for example, can be employed from among various parameters (operating condition parameters) that indicate the operating conditions of the engine 10. One specific example of the engine temperature representative value is a temperature of coolant (coolant temperature) that is detected by the coolant temperature sensor 55.

In the third apparatus, a temperature of coolant that is detected by the coolant temperature sensor 55 is used as the engine temperature representative value. Thus, the engine temperature representative value can be acquired easily and accurately without additionally providing new detection means for determination of fuel properties. As a result, the third apparatus can make a more accurate determination of whether the fuel that is being supplied to the internal combustion engine is a heavy fuel more easily even at low temperatures.

A determination apparatus according to a fourth embodiment of the present invention (which is hereinafter referred to simply as "fourth apparatus") is described. The fourth apparatus of this embodiment is different from the first and second apparatuses only in that the ECU 50 uses the temperature of lubricating oil that has been detected by the oil temperature sensor 56 at start-up of the engine 10 as the engine temperature representative value.

As described above, the ECU 50 sets the threshold value Ch to a value that depends on an engine temperature representative value that has a correlation with the temperature of the engine 10. As the engine temperature representative value, a parameter that has a correlation with the temperature of the engine 10, for example, can be employed from among various parameters (operating condition parameters) that indicate the operating conditions of the engine 10. Another specific example of the engine temperature representative value is a temperature of lubricating oil (oil temperature) that is detected by the oil temperature sensor 56.

In the fourth apparatus, a temperature of lubricating oil that is detected by the oil temperature sensor 56 is used as the engine temperature representative value. Thus, the engine temperature representative value can be acquired easily and accurately without additionally providing new detection means for determination of fuel properties. As a result, the fourth apparatus can make a more accurate determination of whether the fuel that is being supplied to the internal combustion engine is a heavy fuel more easily even at low temperatures.

A determination apparatus according to a fifth embodiment of the present invention (which is hereinafter referred to simply as "fifth apparatus") is described below. The fifth apparatus of this embodiment is different from the first to fourth apparatuses only in that the ECU 50 discards the result of the determination when a refuel sensor detects a refuel operation, and prohibits the execution of the determination when a determination that the fuel that is being supplied to the engine 10 is a heavy fuel has already been made.

In this embodiment, the threshold value Ch that is used to make a determination of whether the fuel that is being supplied to the engine 10 is a heavy fuel is set to a value that depends on an engine temperature representative value that has a correlation with the temperature of the internal combustion engine. Then, a determination that the fuel that is being supplied to the engine 10 is a heavy fuel is made if the ignition fulfillment rate is equal to or greater than the threshold value Ch when feedback control of the ignition timing is performed so that the engine speed can converge to a target speed within a predetermined period after start-up of the engine 10. As a result, the fifth apparatus can make a more accurate determination of whether the fuel that is being supplied to the engine 10 is a heavy fuel even at low temperatures.

The fuel that is supplied to the engine 10 is stored in a container, such as a fuel tank, and supplied to the engine 10 from the container. Thus, the properties of the fuel that is supplied to the engine 10 do not change significantly unless the composition of the fuel in the fuel tank is changed by, for example, refilling the fuel tank with a new fuel.

As described above, in the fifth apparatus, the execution of a new determination process is prohibited when a determination that the fuel that is being supplied to the engine 10 is a "heavy fuel" has already been made. Specifically, when a determination that the fuel is a heavy fuel is made, the data that indicate that the fuel that is now being used is a heavy fuel is maintained (for example, the heavy fuel determination flag is switched to ON as described above with reference to FIG. 1), for example. Thus, once a determination that the fuel is a heavy fuel is made by the fifth apparatus, control suitable for a heavy fuel (for example, air-fuel ratio control suitable for a heavy fuel by ignition timing control means) can be achieved even when a new determination process is not executed every time the engine 10 is started.

When the engine 10 is refueled with a new fuel because the amount of fuel remaining in the fuel tank of the engine 10 has decreased, for example, the properties of the fuel that will be supplied to the engine 10 after that may change. In this case, if the result of the determination of fuel properties in the past is maintained and any control (for example, air-fuel ratio control) is performed based on the result of the determination as described above, the operability and/or exhaust emission of the internal combustion engine may be adversely affected because the control is not suited for the actual fuel properties.

In the fifth apparatus, when the engine 10 is refueled with a new fuel, the result of the determination of fuel properties in the past is discarded. Specifically, the fifth apparatus is applied to an engine 10 that is further equipped with a refuel sensor that detects a refuel operation, and has a control part that discards the result of the determination from the determination process (in the past) when a refuel operation is detected by the refuel sensor. Thus, the fifth apparatus reduces the frequency of determination of fuel properties but still can make an appropriate determination of whether the fuel that is being supplied to the engine 10 is a heavy fuel.

As described above, in the fifth apparatus, the result of the determination of fuel properties in the past is discarded when the engine 10 is refueled with a new fuel. However, when a change in fuel properties is expected even when the engine 10 is not refueled with a new fuel because of volatilization of light components of the fuel in the fuel tank, for example, the opportunities to discard the result of the determination of fuel properties in the past may be increased. Specifically, the result of the determination of fuel properties in the past may be discarded every time the operating time of the engine 10 (when the engine 10 is mounted on a vehicle, the running time or travel distance of the vehicle may be used) reaches a predetermined threshold value, for example.

While some embodiments have been described with reference to the drawings in the foregoing, it should not be interpreted that the scope of the present invention is limited to these illustrative embodiments. The present invention can be modified as appropriate within the scope of the matters that are described in the claims and specification.

What is claimed is:

1. A fuel property determination apparatus for an internal combustion engine, the internal combustion engine including a spark plug, the spark plug including a spark generating portion, the fuel property determination apparatus comprising:
   an electronic control unit configured to:
   (i) perform a feedback control such that an engine speed converges to a target speed by correcting ignition timing during the feedback control, the ignition timing being a timing when the spark generating portion generates a spark,
   (ii) make a determination of a fuel property that fuel supplied to the internal combustion engine is a heavy fuel when an ignition fulfillment rate is equal to or greater than a predetermined threshold value within a predetermined period after the internal combustion engine is started, the ignition fulfillment rate being a ratio of an advance correction amount of the ignition timing to a maximum ignition correction range, the maximum ignition correction range being a maximum range of a correction range in which the ignition timing is corrected during the feedback control, and
   (iii) set the threshold value to a value that depends on a temperature representative value of the internal combustion engine, the temperature representative value being correlated with the temperature of the internal combustion engine.

2. The fuel property determination apparatus according to claim 1, wherein
   the temperature representative value has a positive correlation with the temperature of the internal combustion engine, and
   the electronic control unit is configured to set the threshold value to a greater value as the temperature representative value is smaller.

3. The fuel property determination apparatus according to claim 1, further comprising a coolant temperature sensor configured to detect a temperature of coolant in the internal combustion engine, wherein
   the electronic control unit is configured to use the temperature of coolant as the temperature representative value, the temperature of coolant being detected by the coolant temperature sensor when the internal combustion engine is started.

4. The fuel property determination apparatus according to claim 1, further comprising an oil temperature sensor configured to detect a temperature of lubricating oil in the internal combustion engine, wherein
   the electronic control unit is configured to use the temperature of the lubricating oil as the temperature representative value, the temperature of the lubricating oil being detected by the oil temperature sensor when the internal combustion engine is started.

5. The fuel property determination apparatus according to claim 1, further comprising a refuel sensor configured to detect a refuel operation, wherein
   the electronic control unit is configured to discard a result of the determination of fuel property when a refuel operation is detected by the refuel sensor, and
   the electronic control unit is configured to prohibit an execution of the determination when the fuel is determined as the heavy fuel.

* * * * *